(12) United States Patent
Yoon et al.

(10) Patent No.: US 10,820,858 B2
(45) Date of Patent: Nov. 3, 2020

(54) APPARATUS AND METHOD FOR ESTIMATING BIOMETRIC INFORMATION

(71) Applicant: SAMSUNG ELECTRONICS CO., LTD., Suwon-si (KR)

(72) Inventors: Young Zoon Yoon, Hwaseong-si (KR); Jae Min Kang, Seoul (KR); Yong Joo Kwon, Yongin-si (KR); Seung Woo Noh, Seongnam-si (KR); Sang Yun Park, Hwaseong-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 27 days.

(21) Appl. No.: 15/654,422

(22) Filed: Jul. 19, 2017

(65) Prior Publication Data

US 2018/0098731 A1 Apr. 12, 2018

(30) Foreign Application Priority Data

Oct. 12, 2016 (KR) .......................... 10-2016-0132228

(51) Int. Cl.
*A61B 5/024* (2006.01)
*A61B 5/00* (2006.01)
(Continued)

(52) U.S. Cl.
CPC ............ *A61B 5/681* (2013.01); *A61B 5/0205* (2013.01); *A61B 5/0245* (2013.01);
(Continued)

(58) Field of Classification Search
CPC ....... A61B 5/02; A61B 5/021; A61B 5/02108; A61B 5/024; A61B 5/02438; A61B 5/0402
See application file for complete search history.

(56) References Cited

U.S. PATENT DOCUMENTS

| 4,987,900 A | 1/1991 | Eckerle et al. |
| 5,065,765 A | 11/1991 | Eckerle et al. |

(Continued)

FOREIGN PATENT DOCUMENTS

| CN | 104257371 A | 1/2015 |
| CN | 104970781 A | 10/2015 |

(Continued)

OTHER PUBLICATIONS

Wilson et al. "The Potential Variations Produced by the Heart Beat at the Apices of Einthoven's Triangle". American Heart Journal vol. 7, iss. 2. Dec. 1931. pp. 207-211.*

(Continued)

*Primary Examiner* — Allen Porter
(74) *Attorney, Agent, or Firm* — Sughrue Mion, PLLC

(57) ABSTRACT

An apparatus for estimating biometric information is provided. According to one exemplary embodiment, the apparatus may include a sensor comprising an electrocardiogram (ECG) sensor configured to measure an ECG signal of a user and a pulse wave sensor configured to measure two or more pulse wave signals at two or more measurement sites of the user; and a processor configured to obtain biometric information based on the ECG signal and the two or more pulse wave signals measured by the sensor.

24 Claims, 17 Drawing Sheets

(51) Int. Cl.
  *A61B 5/021* (2006.01)
  *A61B 5/0245* (2006.01)
  *A61B 5/0205* (2006.01)
  *A61B 5/04* (2006.01)
  *A61B 5/0402* (2006.01)

(52) U.S. Cl.
  CPC ...... *A61B 5/02125* (2013.01); *A61B 5/02416* (2013.01); *A61B 5/02438* (2013.01); *A61B 5/0402* (2013.01); *A61B 5/04017* (2013.01); *A61B 5/7207* (2013.01); *A61B 5/7235* (2013.01); *A61B 2560/0468* (2013.01)

(56) References Cited

U.S. PATENT DOCUMENTS

| | | |
|---|---|---|
| 5,265,011 A | 11/1993 | O'Rourke |
| 5,891,022 A | 4/1999 | Pologe |
| 6,095,984 A | 8/2000 | Amano et al. |
| 6,161,038 A | 12/2000 | Schookin et al. |
| 6,475,153 B1 | 11/2002 | Khair et al. |
| 6,571,193 B1 | 5/2003 | Unuma et al. |
| 7,123,363 B2 | 10/2006 | Puttappa et al. |
| 7,231,243 B2 | 6/2007 | Tearney et al. |
| 7,463,796 B2 | 12/2008 | Borgos et al. |
| 7,641,614 B2 | 1/2010 | Asada et al. |
| 7,657,135 B2 | 2/2010 | Borgos et al. |
| 7,737,947 B2 | 6/2010 | Schroeder et al. |
| 7,822,299 B2 | 10/2010 | Borgos et al. |
| 7,925,056 B2 | 4/2011 | Presura et al. |
| 8,032,200 B2 | 10/2011 | Tearney et al. |
| 8,089,465 B2 | 1/2012 | Lutian |
| 8,111,953 B2 | 2/2012 | Borgos et al. |
| 8,217,897 B2 | 7/2012 | Lutian |
| 8,277,384 B2 | 10/2012 | Fine |
| 8,313,439 B2 | 11/2012 | McCombie et al. |
| 8,343,062 B2 | 1/2013 | Fortin et al. |
| 8,343,063 B2 | 1/2013 | Borgos |
| 8,360,985 B2 | 1/2013 | Borgos |
| 8,467,636 B2 | 6/2013 | Borgos et al. |
| 8,496,595 B2 | 7/2013 | Jornod |
| 8,808,188 B2 | 8/2014 | Banet et al. |
| 8,868,149 B2 | 10/2014 | Eisen et al. |
| 8,954,135 B2 | 2/2015 | Yuen et al. |
| 9,097,516 B2 | 8/2015 | Hotta et al. |
| 9,149,216 B2 | 10/2015 | Eisen et al. |
| 9,277,868 B2 | 3/2016 | Borgos et al. |
| 9,282,931 B2 | 3/2016 | Tearney et al. |
| 9,326,711 B2 | 5/2016 | Kracker et al. |
| 9,510,758 B2 | 12/2016 | Warger, II et al. |
| 9,596,990 B2 | 3/2017 | Park et al. |
| 9,603,524 B2 | 3/2017 | Park et al. |
| 9,636,041 B2 | 5/2017 | Zalevsky et al. |
| 9,668,672 B2 | 6/2017 | Zalevsky et al. |
| 9,704,050 B2 | 7/2017 | Lee et al. |
| 10,357,165 B2 | 7/2019 | Yoon |
| 2002/0007125 A1 | 1/2002 | Hickey |
| 2002/0095092 A1 | 7/2002 | Kondo et al. |
| 2003/0013976 A1 | 1/2003 | Freund et al. |
| 2004/0186387 A1 | 9/2004 | Kosuda et al. |
| 2005/0228297 A1 | 10/2005 | Banet et al. |
| 2007/0078308 A1 | 4/2007 | Daly |
| 2007/0163353 A1 | 7/2007 | Lec et al. |
| 2007/0265533 A1 | 11/2007 | Tran |
| 2007/0276262 A1* | 11/2007 | Banet .............. A61B 5/02255 600/485 |
| 2007/0276632 A1* | 11/2007 | Banet .............. A61B 5/021 702/187 |
| 2008/0071180 A1 | 3/2008 | Borgos |
| 2008/0146952 A1 | 6/2008 | Presura et al. |
| 2008/0181556 A1 | 7/2008 | Borgos et al. |
| 2008/0183053 A1 | 7/2008 | Borgos et al. |
| 2008/0228089 A1 | 9/2008 | Cho et al. |
| 2009/0069698 A1 | 3/2009 | Bae et al. |
| 2009/0073461 A1 | 3/2009 | Borgos et al. |
| 2009/0209834 A1 | 8/2009 | Fine |
| 2009/0209871 A1 | 8/2009 | Ueki et al. |
| 2009/0326393 A1 | 12/2009 | Sethi et al. |
| 2010/0022861 A1 | 1/2010 | Cinbis et al. |
| 2010/0049059 A1 | 2/2010 | Ha et al. |
| 2010/0145171 A1 | 6/2010 | Park et al. |
| 2010/0160798 A1 | 6/2010 | Banet et al. |
| 2010/0168589 A1 | 7/2010 | Banet et al. |
| 2010/0210930 A1 | 8/2010 | Saylor |
| 2010/0210956 A1 | 8/2010 | Im |
| 2010/0324384 A1 | 12/2010 | Moon et al. |
| 2011/0021931 A1 | 1/2011 | Borgos et al. |
| 2011/0172505 A1 | 7/2011 | Kim et al. |
| 2011/0208066 A1 | 8/2011 | Gnadinger |
| 2012/0025185 A1 | 2/2012 | Kasamatsu |
| 2012/0108956 A1 | 5/2012 | Warger, II et al. |
| 2012/0130215 A1 | 5/2012 | Fine et al. |
| 2012/0130253 A1 | 5/2012 | Nadkarni et al. |
| 2012/0130260 A1 | 5/2012 | Borgos et al. |
| 2012/0136261 A1 | 5/2012 | Sethi et al. |
| 2012/0143066 A1 | 6/2012 | Antonelli et al. |
| 2012/0191001 A1 | 7/2012 | Segman |
| 2013/0046192 A1 | 2/2013 | Lin et al. |
| 2013/0131475 A1 | 5/2013 | Eisen et al. |
| 2013/0144137 A1 | 6/2013 | Zalevsky et al. |
| 2013/0190630 A1 | 7/2013 | Borgos |
| 2013/0218025 A1 | 8/2013 | Tverskoy |
| 2013/0245456 A1 | 9/2013 | Ferguson, Jr. et al. |
| 2014/0012146 A1 | 1/2014 | Fukuda |
| 2014/0066788 A1 | 3/2014 | Mukkamala et al. |
| 2014/0066793 A1 | 3/2014 | Mukkamala et al. |
| 2014/0081153 A1 | 3/2014 | Kuno |
| 2014/0107493 A1 | 4/2014 | Yuen et al. |
| 2014/0125491 A1 | 5/2014 | Park et al. |
| 2014/0127996 A1 | 5/2014 | Park et al. |
| 2014/0148658 A1 | 5/2014 | Zalevsky et al. |
| 2014/0200423 A1 | 7/2014 | Eisen et al. |
| 2014/0288435 A1 | 9/2014 | Richards et al. |
| 2015/0105638 A1 | 4/2015 | Eisen et al. |
| 2015/0117015 A1 | 4/2015 | Roh et al. |
| 2015/0119654 A1* | 4/2015 | Martin .............. A61B 5/0059 600/301 |
| 2015/0119725 A1 | 4/2015 | Martin et al. |
| 2015/0126820 A1* | 5/2015 | Muhlsteff .............. A61B 5/029 600/301 |
| 2015/0323311 A1 | 11/2015 | Muijs et al. |
| 2016/0058300 A1 | 3/2016 | Yoon et al. |
| 2016/0066790 A1 | 3/2016 | Shcherbakov et al. |
| 2016/0081572 A1* | 3/2016 | Hong .............. A61B 5/6898 600/301 |
| 2016/0103985 A1 | 4/2016 | Shim et al. |
| 2016/0106325 A1 | 4/2016 | Kang et al. |
| 2016/0106327 A1 | 4/2016 | Yoon et al. |
| 2016/0106333 A1 | 4/2016 | Kang et al. |
| 2016/0113589 A1 | 4/2016 | Yoon |
| 2016/0157736 A1 | 6/2016 | Huang et al. |
| 2016/0192845 A1 | 7/2016 | Warger et al. |
| 2016/0198961 A1 | 7/2016 | Homyk et al. |
| 2016/0206251 A1 | 7/2016 | Kwon et al. |
| 2016/0256116 A1 | 9/2016 | Baik et al. |
| 2016/0256117 A1 | 9/2016 | Baik et al. |
| 2016/0278645 A1 | 9/2016 | Yoon |
| 2016/0278718 A1 | 9/2016 | Fujii et al. |
| 2016/0287109 A1 | 10/2016 | Shim et al. |
| 2016/0357154 A1 | 12/2016 | Shim et al. |
| 2017/0017858 A1 | 1/2017 | Roh et al. |
| 2017/0049340 A1 | 2/2017 | Cho et al. |
| 2017/0055855 A1 | 3/2017 | Yoon |
| 2017/0065184 A1 | 3/2017 | Barak |
| 2017/0105679 A1 | 4/2017 | Gil |
| 2017/0112395 A1 | 4/2017 | Kim et al. |
| 2017/0135636 A1 | 5/2017 | Park et al. |
| 2017/0150930 A1 | 6/2017 | Shikii et al. |
| 2017/0172510 A1 | 6/2017 | Homyk et al. |
| 2017/0209047 A1 | 7/2017 | Zalevsky et al. |
| 2017/0245796 A1 | 8/2017 | Zalevsky et al. |

(56) References Cited

U.S. PATENT DOCUMENTS

| | | |
|---|---|---|
| 2017/0251926 A1 | 9/2017 | Yoon et al. |
| 2017/0319146 A1 | 11/2017 | Park et al. |

FOREIGN PATENT DOCUMENTS

| | | | |
|---|---|---|---|
| DE | 102010014761 A1 | 10/2011 | |
| EP | 0755221 B1 | 10/2001 | |
| EP | 1 204 370 B1 | 4/2008 | |
| EP | 3072441 A1 | 9/2016 | |
| JP | 11-155826 A | 6/1999 | |
| JP | 2000-166885 A | 6/2000 | |
| JP | 2003-532478 A | 11/2003 | |
| JP | 3769524 B2 | 4/2006 | |
| JP | 2008-295576 A | 12/2008 | |
| JP | 4506849 B2 | 7/2010 | |
| JP | 4614184 B2 | 1/2011 | |
| JP | 4645259 B2 | 3/2011 | |
| JP | 4848732 B2 | 12/2011 | |
| JP | 2012-57962 A | 3/2012 | |
| JP | 2012-161507 A | 8/2012 | |
| JP | 2012-187300 A | 10/2012 | |
| JP | 2012202776 A | 10/2012 | |
| JP | 2013-509225 A | 3/2013 | |
| JP | 2014-23031 A | 2/2014 | |
| JP | 5528816 B2 | 6/2014 | |
| JP | 2014240782 A | 12/2014 | |
| JP | 2015502197 A | 1/2015 | |
| KR | 10-0610813 B1 | 8/2006 | |
| KR | 10-0650044 B1 | 11/2006 | |
| KR | 10-2008-0073988 A | 8/2008 | |
| KR | 10-2009-0052442 A | 5/2009 | |
| KR | 10-2010-0060141 A | 6/2010 | |
| KR | 10-2010-0065084 A | 6/2010 | |
| KR | 10-1007354 B1 | 1/2011 | |
| KR | 1020110025100 A | 3/2011 | |
| KR | 10-1040598 B1 | 6/2011 | |
| KR | 10-1058152 B1 | 8/2011 | |
| KR | 10-1065615 B1 | 9/2011 | |
| KR | 10-2012-0057813 A | 6/2012 | |
| KR | 10-1310464 B1 | 9/2013 | |
| KR | 10-2014-0024845 A | 3/2014 | |
| KR | 10-1503604 B1 | 3/2015 | |
| KR | 10-1564066 B1 | 10/2015 | |
| KR | 101560287 B1 | 10/2015 | |
| KR | 10-2016-0041553 A | 4/2016 | |
| KR | 10-2016-0088127 A | 7/2016 | |
| KR | 10-2016-0107007 A | 9/2016 | |
| KR | 10-2016-0108081 A | 9/2016 | |
| KR | 1020170104361 A | 9/2017 | |
| KR | 1020170124943 A | 11/2017 | |
| WO | 2015129949 A1 | 9/2015 | |

OTHER PUBLICATIONS

U.S. Non-Final OA dated Aug. 24, 2017 issued by the USPTO in counterpart U.S. Appl. No. 14/844,437.
U.S. Non-Final OA dated Sep. 27, 2017 issued by the USPTO in counterpart U.S. Appl. No. 14/961,145.
U.S. Non-Final OA dated Nov. 1, 2017 issued by the USPTO in counterpart U.S. Appl. No. 14/862,288.
U.S. Non-Final OA dated Sep. 26, 2017 issued by the USPTO in counterpart U.S. Appl. No. 15/068,760.
Anonymous, "Central Venous Pressure Waveforms", Section 3: Anesthesia Management, Part B: Monitoring, Chapter 30: Cardiovascular Monitoring, 1979, http://web.squ.edu.om/med-Lib/MED_CD/E_CDs/anesthesia/site/content/v03/030275r00.HTM; 4 pages total.
Kurylyak et al., "A Neural Network-based Method for Continuous Blood Pressure Estimation from a PPG Signal", Conference (I2MTC), 2013 IEEE International, (4 pages total).
Office Action dated Dec. 14, 2018 issued by the U.S. Patent and Trademark Office in U.S. Appl. No. 14/884,019.
Advisory Action dated Dec. 19, 2017 issued by the U.S. Patent and Trademark Office in U.S. Appl. No. 15/068,760.
Office Action dated Jun. 15, 2018 by the U.S. Patent and Trademark Office in U.S. Appl. No. 14/844,437.
Restriction Requirement dated Sep. 6, 2018 issued by the USPTO in counterpart U.S. Appl. No. 14/884,019.
Notice of Allowance dated Oct. 24, 2018, issued by United States Patent and Trademark Office in U.S. Appl. No. 15/068,760.
Office Action dated Aug. 2, 2018 by the United States Patent and Trademark Office in U.S. Appl. No. 14/862,288.
Office Action dated Jul. 16, 2018 by the United States Patent and Trademark Office in U.S. Appl. No. 15/068,760.
Office Action dated Jul. 26, 2018 by the United States Patent and Trademark Office in U.S. Appl. No. 14/833,221.
Office Action dated Aug. 6, 2018 by the United States Patent and Trademark Office in U.S. Appl. No. 14/818,420.
Office Action dated Jan. 30, 2018 by the United States Patent and Trademark Office in U.S. Appl. No. 15/068,760.
Final Office Action dated Feb. 28, 2018 by the USPTO in counterpart U.S. Appl. No. 14/961,145.
Final Office Action dated Mar. 8, 2018 by the USPTO in counterpart U.S. Appl. No. 14/844,437.
Restriction Requirement dated Mar. 8, 2018 by the USPTO in counterpart U.S. Appl. No. 14/833,221.
Notice of Allowance dated Nov. 7, 2018, issued by United States Patent and Trademark Office in U.S. Appl. No. 14/844,437.
Notice of Allowance dated Nov. 15, 2018, issued by United States Patent and Trademark Office in U.S. Appl. No. 14/818,420.
Office Action dated May 23, 2018 by United States Patent and Trademark Office, in U.S. Appl. No. 14/862,288.
Office Action dated May 25, 2018 by United States Patent and Trademark Office, in U.S. Appl. No. 14/961,145.
Office Action dated Feb. 15, 2019 issued by the U.S. Patent and Trademark Office in U.S. Appl. No. 14/961,145.
Notice of Allowance dated Mar. 4, 2019 issued by the U.S. Patent and Trademark Office in U.S. Appl. No. 14/818,420.
Final Office Action dated Mar. 7, 2019 issued by the U.S. Patent and Trademark Office in U.S. Appl. No. 14/833,221.
Notice of Allowance dated Mar. 18, 2019 issued by the U.S. Patent and Trademark Office in U.S. Appl. No. 15/068,760.
Non-Final Office Action dated Mar. 22, 2019 issued by the U.S. Patent and Trademark Office in U.S. Appl. No. 14/862,288.
Communication (Non-Final Office Action) dated Dec. 22, 2017 issued by the USPTO in counterpart U.S. Appl. No. 14/818,420.
Zhang et al., "A LabVIEW Based Measure System for Pulse Wave Transit Time"; Proceedings of the 5th International Conference on Information Technology and Application in Biomedicine, in conjunction with The 2nd International Symposium & Summer School on Biomedical and Health Engineering; May 30-31, 2008; 4 pgs. Total, pp. 477-480.
Yan et al., "Noninvasive Estimation of Blood Pressure Using Photophlethysmographic Signals in the Period Domain"; Proceedings of the 2005 IEEE Engineering in Medicine and Biology 27th Annual Conference; Sep. 1-4, 2005; 2 pgs. total.
Fortino et al., "PPG-based Methods for Non Invasive and Continuous Blood Pressure Measurement: an Overview and Development Issues in Body Sensor Networks"; IEEE; 2010; 4 pgs. total.
Kurylyak, et al., "A Neural Network-based Method for Continuous Blood Pressure Estimation from a PPG Signal"; Instrumentation and Measurement Technology Conference (I2MTC); May 6-9, 2013; 4pgs. Total, pp. 280-283.
Teng et al., "Continuous and Noninvasive Estimation of Arterial Blood Pressure Using Photoplethysmographic Approach"; Proceedings of the 25th Annual International Conference of the IEEE EMBS; Sep. 17-21, 2003; 4 pgs. Total, pp. 3153-3156.
Young-Zoon Yoon.,"Study on cardiovascular system with blood pressure waveform and heart rate variability", A Dissertation Submitted to the Faculty of Seoul National University in Partial Fulfillment of the Requirements for the Degree of Doctor of Philosophy, School of Physics, Graduate School, Seoul National University, 2005, (210 Pages Total).
Chen et al., "Estimation of Central Aortic Pressure Waveform by Mathematical Transformation of Radial Tonometry Pressure; Validation of Generalized Transfer Function", 1997: 95, 1827-36, 12 pages total, American Heart Association.

(56) References Cited

OTHER PUBLICATIONS

O'Rourke et al., "Pulse wave analysis", Research Methods in Human Cardiovascular Pharmacology, 2001, Clinical Pharmacology, Blackwell Science Ltd Br J Clin Pharmacol: 51, pp. 507-522, 16 pages total.

Aymen A. Awad et al., "How Does the Plethysmogram Derived from the Pulse Oximeter Relate to Arterial Blood Pressure in Coronary Artery Bypass Graft Patients?"; Anesth Analg, 93; 2001; pp. 1466-1471; 6 pgs. total.

Satomi Suzuki, et al., "Cuffless and Non-invasive Systolic Blood Pressure Estimation for Aged Class by Using Photoplethysmograph"; 30th Annual International IEEE Embs Conference; Aug. 20-24, 2008; pp. 1327-1330; 4 pgs. total.

Arata Suzuki et al., "Feature Selection Method for Estimating Systolic Blood Pressure Using the Taguchi Method"; IEEE Transactions on Industrial Informatics; vol. 10; No. 2; May 2014; pp. 1077-1085; 9 pgs. total.

Y. Kurylyak et al., "Photoplethysmogram-based Blood Pressure Evaluation using Kalman Filtering and Neural Networks"; Medical Measurements and Applications Proceedings (MeMeA), 2013 IEEE International Symposium; May 4, 2013; 5 pgs. total.

Yevgeny Beiderman et al., "Remote estimation of blood pulse pressure via temporal tracking of reflected secondary speckles pattern"; Journal of Biomedical Optics; vol. 15; No. 6; Nov./Dec. 2010; pp. 061707-1-061707-7; 7 pgs. total.

Yu.N. Kul'Chin et al., "Correlation method for processing speckles of signals from signal-fibre multimode interferometers by using charge-coupled devices"; Optical Fibres and Waveguides; Quantum Electronics; vol. 36; No. 4; 2006; pp. 339-342; 5 pgs. total.

Enric Monte-Moreno., "Non-invasive estimate of blood glucose and blood pressure from a photoplethysmograph by means of machine learning techniques", Artificial Intelligence in Medicine, vol. 53, 2011, pp. 127-138.

Communication dated Aug. 30, 2016 issued by the European Patent Office in counterpart European Patent Application No. 16158751.4.

Ramakrishna Mukkamala et al., "Towards Ubiquitous Blood Pressure Monitoring via Pulse Transit Time: Theory and Practice", IEEE Trans Biomed Eng. Aug. 2015 ; 62(8), pp. 1879-1901, 48 pages total.

Qing Liu et al., "Attenuation of Systolic Blood Pressure and Pulse Transit Time Hysteresis During Exercise and Recovery in Cardiovascular Patients", IEEE Transactions on Biomedical Engineering, vol. 61, No. 2, Feb. 2014, pp. 346-352.

R. A. Payne et al., "Pulse transit time measured from the ECG: an unreliable marker of beat-to-beat blood pressure", J Appl Physiol, the American Physiological Society 100, 2006, pp. 136-141.

Communication from United States Patent and Trademark Office dated Jun. 28, 2017, in U.S. Appl. No. 14/844,437.

Communication from United States Patent and Trademark Office dated Mar. 20, 2017, in U.S. Appl. No. 14/818,420.

Communication from United States Patent and Trademark Office dated Jun. 16, 2017, in U.S. Appl. No. 14/818,420.

Communication from United States Patent and Trademark Office dated Apr. 17, 2017, in U.S. Appl. No. 15/068,760.

Jianjun Qiu et al; "Spatiotemporal laser speckle contrast analysis for blood flow imaging with maximized speckle contrast"; Journal of Biomedical Optics; vol. 15; No. 1; Jan./Feb. 2010; pp. 016003-1-016003-5; 5pgs. total.

Dr. S. Shah et al; "Optoelectronic blood pressure estimation: A novel principle for blood pressure measurement"; Tarilian Laser Technologies; (http://www.tarilian-lasertechnologies.com/press/tlt-at-esh2012.php); 2012; 4 pgs. total.

"Tarilian Laser Technologies achieves greatest technological advance in blood pressure measurement for 130 years"; (http://www.tarilian-lasertechnologies.com/press/pr111201.php); Tarilian Laser Technologies; Dec. 7, 2011; 6 pgs. total.

Communication dated Dec. 14, 2017, issued by the European Patent Office in counterpart European Application No. 17172684.7.

Final Office Action dated Jun. 20, 2019 issued by the U.S. Patent and Trademark Office in U.S. Appl. No. 14/884,019.

Notice of Allowance dated Apr. 24, 2019, issued by the U.S. Patent and Trademark Office in U.S. Appl. No. 14/961,145.

Notice of Allowance dated Jul. 31, 2019 issued by the USPTO in U.S. Appl. No. 14/862,288.

Notice of Allowance dated Nov. 6, 2019 issued by the United States Patent and Trademark Office in U.S. Appl. No. 14/844,437.

Non-Final Office Action dated Jan. 10, 2020 issued by the U.S. Patent and Trademark Office in U.S. Appl. No. 14/833,221.

Notice of Allowance dated Apr. 8, 2020 issued by the U.S. Patent and Trademark Office is U.S. Appl. No. 14/884,019.

Vaz et al. "Laser Speckle Imaging to Monitor Microvascular Blood Flow: A Review.", IEEE Reviews in BME, vol. 9, 2016, pp. 106-120.

Gubarev et al. "Speckle Pattern Processing by Digital Image Correlation.", MATEC Web of Conferences 2016, 6 pages.

\* cited by examiner

APPARATUS AND METHOD FOR ESTIMATING BIOMETRIC INFORMATION

CROSS-REFERENCE TO RELATED APPLICATION(S)

This application claims priority from Korean Patent Application No. 10-2016-0132228, filed on Oct. 12, 2016 in the Korean Intellectual Property Office, the entire disclosure of which is incorporated herein by reference in its entirety.

BACKGROUND

1. Field

Apparatuses and methods consistent with exemplary embodiments relate to estimating biometric information, and more specifically, estimating biometric information on the basis of biometric signals obtained at multiple sites of a subject to be examined.

2. Description of Related Art

As a general blood pressure measurement method, a pressure cuff method is used. This method is a non-continuous measurement method by which a blood pressure is measured by tightening a cuff around blood vessels to a point to reach the maximum blood pressure and loosening the cuff. Also, the method is not suitable for use in a wristwatch type measurement device due to the structure, such as a pressure pump. Recently, a non-pressure cuffless-type blood pressure measurement method has been studied. A general cuffless blood pressure measurement method uses a correlation between a pulse transit time (PTT) and a blood pressure, for example, a pulse wave or an electrocardiogram (ECG) measured at two different sites.

SUMMARY

According to an aspect of an exemplary embodiment, there is provided an apparatus for estimating biometric information including: a sensor including an electrocardiogram (ECG) sensor configured to measure an ECG signal of a user and a pulse wave sensor configured to measure two or more pulse wave signals at two or more measurement sites of the user; and a processor configured to receive the ECG signal and the two or more pulse wave signals from the sensor and obtain biometric information based on the received ECG and two or more pulse wave signals.

The apparatus may further include a main body and a strap connected to the main body and formed to be flexible to wrap around at least one of the two or more measurement sites, wherein the sensor is mounted in the main body or the strap.

The two or more measurement sites of the user may include a first measurement site and a second measurement site of the user. The ECG sensor may include a first electrode disposed at a first position of the apparatus to be in contact with the first measurement site of the user and a second electrode disposed at a second position of the apparatus to be in contact with the second measurement site of the user.

The pulse wave sensor may include: a first pulse wave sensor configured to emit light to the first measurement site, detect the light returning from the first measurement site, and obtain a first pulse wave signal from the light detected by the first pulse wave sensor; and a second pulse wave sensor configured to emit light to the second measurement site, detect the light returning from the second measurement site, and obtain a second pulse wave signal from the light detected by the second pulse wave sensor.

The apparatus may further include a display configured to output the biometric information according to a control signal of the processor.

The processor may include a transit time calculator configured to determine at least three pulse transit times (PTTs) based on the received ECG and two or more pulse wave signals, and a first estimator configured to apply the three or more PTTs to a first estimation model to obtain first biometric information.

The processor may include a pulse wave analyzer configured to extract, from waveforms of the two or more pulse wave signals, reflected wave characteristic information indicating an impact of reflected waves of the two or more pulse wave signals on a change in waveform of the two or more pulse wave signals, and a second estimator configured to apply the extracted reflected wave characteristic information to a second estimation model to obtain second biometric information.

The pulse wave analyzer may be further configured to extract feature points from the two or more pulse wave signals, and extract the reflected wave characteristic information which comprises one or more first PTTs calculated using the feature points of different pulse wave signals of the two or more pulse wave signals and one or more second PTTs calculated using the feature points of a same pulse wave signal of the two or more pulse wave signals.

When a result is output by applying the extracted reflected wave characteristic information to the second estimation model, the second estimator is further configured to obtain the second biometric information based on the output result and the first biometric information.

The first biometric information may be a diastolic blood pressure and the second biometric information may be a systolic blood pressure.

The processor may be further configured to generate an estimation model for estimating the biometric information based on personal information input by the user, and the personal information may include one or more of height, weight, sex, age, and a health condition of the user.

The processor may include a calibrator configured to obtain vascular resistance information based on waveforms of the two or more pulse wave signals and calibrate the biometric information based on the vascular resistance information.

The apparatus may further include a communication interface configured to receive reference biometric information from an external apparatus. The processor may include a calibrator configured to calibrate the biometric information based on the reference biometric information.

The processor may be further configured to obtain the biometric information while the external apparatus obtains the reference biometric information of the user.

The calibrator is further configured to calibrate at least one of a value of the biometric information, two or more pulse transit times (PTTs) calculated using the ECG signal and the two or more pulse wave signals, and an estimation model for estimating the biometric information.

The external apparatus may include a cuff-type blood pressure estimating apparatus and the reference biometric information includes at least one of a cuff blood pressure estimated by the cuff-type blood pressure estimating apparatus and cuff pressure information.

According to an aspect of another exemplary embodiment, there is provided a method of estimating biometric information including: measuring a user's electrocardiogram (ECG) signal; measuring two or more pulse wave signals from two or more measurement sites of the user; and obtaining biometric information based on the ECG signal and the two or more pulse wave signals.

The obtaining the biometric information may include determining at least three pulse transit times (PTTs) based on the ECG signal and the two or more pulse wave signals and applying the at least three PTTs to a first estimation model to obtain first biometric information.

The obtaining the biometric information may include extracting, from waveforms of the two or more pulse wave signals, reflected wave characteristic information indicating an impact of reflected waves of the two or more pulse wave signals on a change in waveform of the two or more pulse wave signals and applying the extracted reflected wave characteristic information to a second estimation model to obtain second biometric information.

The extracting the reflected wave characteristic information may include extracting feature points from the two or more pulse wave signals and extracting the reflected wave characteristic information which includes one or more first PTTs calculated using the feature points of different pulse wave signals of the two or more pulse wave signals and one or more second PTTs calculated using the feature points of a same pulse wave signal of the two or more pulse wave signals.

When a result is output by applying the extracted reflected wave characteristic information to the second estimation model, the second biometric information may be obtained based on the output result and the first biometric information.

The method may further include: receiving personal information input by the user, the personal information including one or more of height, weight, sex, age, and a health condition of the user; and generating an estimation model for estimating the biometric information based on the received personal information.

The method may further include: obtaining vascular resistance information based on waveforms of the two or more pulse wave signals; and calibrating the biometric information based on the vascular resistance information to correct an error in the biometric information.

The method may further include: receiving reference biometric information from an external apparatus; and calibrating the biometric information based on the received reference biometric information.

The calibrating the biometric information may include calibrating at least one of a value of the biometric information, two or more pulse transit times (PTTs) calculated using the ECG signal and the two or more pulse wave signals, and an estimation model for estimating the biometric information.

The reference biometric information may include at least one of a cuff blood pressure estimated by a cuff-type blood pressure estimating apparatus included in the external apparatus and cuff pressure information.

According to an aspect of another exemplary embodiment, there is provided an apparatus for obtaining blood pressure information including: a plurality of sensors configured to detect an electrocardiogram (ECG) signal of a user and detect a plurality of photoplethysmography (PPG) signals at different measurement sites of the user, the plurality of PPG signals including a first PPG signal and a second PPG signal; and a processor configured to determine a first differential pulse transit time (DPTT) between the ECG signal and the first PPG signal, a second DPTT between the ECG signal and the second PPG signal, and a third DPTT between the first PPG signal and the second PPG signal, and determine a blood pressure level of the user based on the first DPTT, the second DPTT, and the third DPTT.

The processor may be further configured to receive information of physical characteristics of the user, set a maximum level and a minimum level for the blood pressure level to be determined, and determine the blood pressure level based on the first DPTT, the second DPTT, the third DPTT, and the physical characteristics of the user.

The physical characteristics may include one or more of height, weight, sex and age of the user.

BRIEF DESCRIPTION OF THE DRAWINGS

The above and/or other aspects will be more apparent by describing certain exemplary embodiments, with reference to the accompanying drawings, in which.

DETAILED DESCRIPTION

Figure 1A:
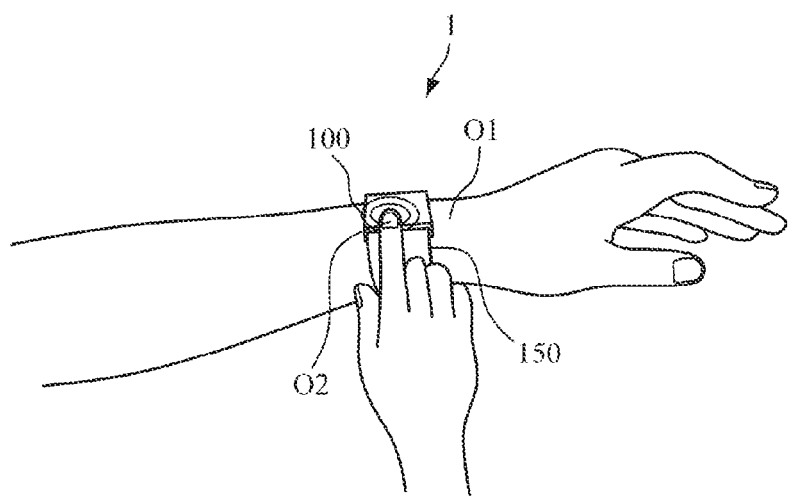
FIGS. 1A and 1B are diagrams illustrating the configuration of an apparatus for estimating biometric information according to an exemplary embodiment of the present invention.

Exemplary embodiments are described in greater detail below with reference to the accompanying drawings.

In the following description, like drawing reference numerals are used for like elements, even in different drawings. The matters defined in the description, such as detailed construction and elements, are provided to assist in a comprehensive understanding of the exemplary embodiments. However, it is apparent that the exemplary embodiments can be practiced without those specifically defined matters. In the following description, a detailed description of known functions and configurations incorporated herein will be omitted when it may obscure the subject matter with unnecessary detail.

It will be understood that, although the terms first, second, etc. may be used herein to describe various elements, these elements should not be limited by these terms. These terms are only used to distinguish one element from another. Also, the singular forms are intended to include the plural forms as well, unless the context clearly indicates otherwise. In the specification, unless explicitly described to the contrary, the words "comprise" and "includes" and their variations such as "comprises," "comprising," "includes," and "including," will be understood to imply the inclusion of stated elements but not the exclusion of any other elements. Terms such as " . . . unit" and "module" denote units that process at least one function or operation, and they may be implemented by using hardware, software, or a combination of hardware and software.

Figure 1B:
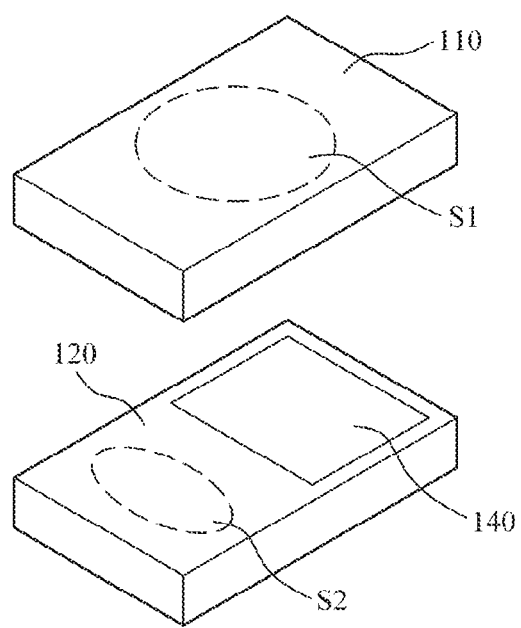

FIGS. 1A and 1B are diagrams illustrating the configuration of an apparatus for estimating biometric information according to an exemplary embodiment.

The apparatus 1 for estimating biometric information may be a wearable device which can be worn on a user's body part. In addition, the form of the apparatus may not be particularly limited and may be manufactured in various types, such as a wristwatch type, a bracelet type, a ring type, a glass-type, a hairband type, and the like. However, as shown in FIGS. 1A and 1B, the apparatus 1 will be described as having a wristwatch-type for convenience of description.

Referring to FIGS. 1A and 1B, the apparatus 1 for estimating biometric information includes a main body 100 and a strap 150 connected to the main body 100 and formed to be flexible to wrap around a user's wrist.

Various modules for performing various functions for estimating biometric information may be mounted in the main body 100. For example, the main body 100 may include a sensor module configured to measure bio-signals at a plurality of measurement sites O1 and O2 and a processing module configured to estimate biometric signal based on the measured biometric signals.

From the biometrical signals, the apparatus 1 may acquire biometric information such as blood pressure information including a diastolic blood pressure and a systolic blood pressure. However, the biometric information is not limited to blood pressure information and may include a vascular age, a degree of arterial stiffness, an aortic pressure waveform, a stress index, a degree of fatigue, and the like. In addition, the biometric signals measured at a plurality of sites O1 and O2 of a subject by the sensor module may include an electrocardiogram (ECG) signal, a photoplethysmography (PPG) signal (hereinafter, will be referred to as a "pulse wave signal"), etc.

For example, at least a part of the sensor module may be disposed at position S1 of a lower part 110 of the main body 100. Thus, when the user wears the apparatus 1, the lower part 110 of the main body 100 comes into contact with the upper part of the user's wrist (i.e., the back of the user's hand) including a first measurement site O1 so that the sensor module measures a biometric signal at the first measurement site O1 (e.g., an upper part O1 of the wrist through which venous blood or capillary blood passes). In addition, at least a part of the sensor module may be disposed at a specific position S2 of the upper part 120 of the main body 100 so as to measure a biometric signal at a second measurement site O2 (e.g., a finger O2 of the hand on which the apparatus 1 is not worn).

In addition, a display module 140 may be mounted in the upper part 120 of the main body 100 so as to display the biometric signal measured by the sensor module or a processing result of the processing module. In this case, the display module 140 may be implemented to allow touch input, in addition to displaying processing result, so that the display module 140 can interact with the user. In addition, a communication module to be connected to an external device using a wired or wireless connection technology to transmit and receive various data necessary for biometric information estimation may be included. However, the embodiment is not limited to the above modules, and various modules for performing various functions may be included.

In addition, although the sensor module is described as being mounted in the main body 100, the position of the sensor module is not limited thereto, and at least a part of the sensor module may be placed at the strap 150 so as to acquire a biometric signal at a measurement site at which the radial artery passes. For example, the sensor module for acquiring a biometric signal at the first measurement site may be disposed on one surface of the strap 150 which is in contact with the first measurement site at which the radial artery passes, and the sensor module for acquiring a biometric signal at the second measurement site may be disposed on the other surface of the strap 150 which is in contact with a finger of the other hand that is the second measurement site. Alternatively, the sensor module for acquiring a biometric signal at the first measurement site may be mounted in the strap 150, and the sensor module for acquiring a biometric signal at the second measurement site may be mounted in the upper part 120 of the main body 100.

Figure 2:
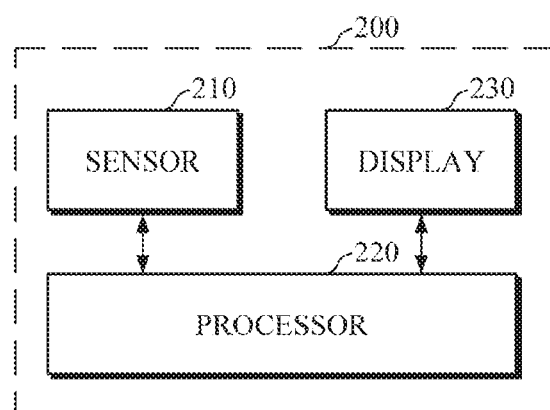
FIG. 2 is a block diagram illustrating an apparatus for estimating biometric information according to an exemplary embodiment.
Figure 3:
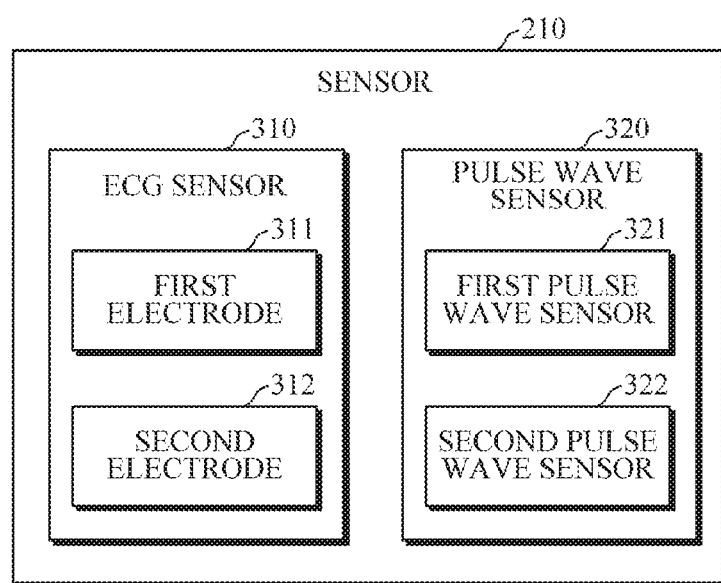
FIG. 3 is a block diagram illustrating a sensor of the apparatus for estimating biometric information according to an exemplary embodiment.

FIG. 2 is a block diagram illustrating an apparatus for estimating biometric information according to an exemplary embodiment. FIG. 3 is a block diagram illustrating a sensor of the apparatus for estimating biometric information according to an exemplary embodiment. The apparatus 200 for estimating biometric information according to the present exemplary embodiment may be one exemplary embodiment of the apparatus 1 illustrated in FIGS. 1A and 1B.

Referring to FIGS. 1A, 1B, and 2, the apparatus for estimating biometric information includes a sensor 210, a processor 220, and a display 230.

The sensor 210 may include one or more sensors to acquirer biometric signals from a plurality of measurement sites of a user. The sensor 210 may be mounted in the main body 100 or the strap 150. Hereinafter, for convenience of description, the sensor 210 will be described as being mounted in the main body 100. The sensor 210 may include an ECG sensor 310 and a pulse wave sensor 320 to measure pulse wave signals at two or more measurement sites.

For example, the ECG sensor 310 may include a first electrode 311 and a second electrode 312. The first electrode 311 may be disposed at a specific position S1 on the lower part 110 of the main body 100 such that the first electrode 311 is in contact with a first measurement site O1 when the lower part 110 of the main body 100 is in close contact with a subject to be measured. In addition, the second electrode 312 may be disposed at a specific position S2 on the upper part 120 of the main body 100 which is in contact with a second measurement site O2 of the subject to be measured.

In this case, the first electrode 311 may be a positive (+) electrode and the second electrode 312 may be a negative (−) electrode.

The pulse wave sensor 320 may include two or more pulse wave sensors to measure two or more pulse wave signals of the user. For example, referring to FIG. 3, the pulse wave sensor 320 may include a first pulse wave sensor 321 and a second pulse wave sensor 322 to measure pulse wave signals at two sites of the subject. The first pulse wave sensor 321 may be disposed at a specific position S1 on the lower part 110 of the main body 100 which is in contact with the first measurement site O1 and may measure a pulse wave signal from the first measurement site O1. In addition, the second pulse wave sensor 322 may be disposed at a specific position S2 on the upper part 120 of the main body which is in contact with the second measurement site O2 and may measure a pulse wave signal from the second measurement site O2. In this case, the first pulse wave sensor 321 and the second pulse wave sensor 322 each may include a light source configured to emit light and a detector configured to detect light reflected back from the user.

When the sensor 210 receives a control signal from the processor 220 and the second measurement site O2 of the user comes in contact with the specific position S2 of the upper part 120 of the main body 100, the ECG sensor 310 is operated to measure an ECG and the first pulse wave sensor 321 and the second pulse wave sensor 322 are operated to measure a first pulse wave signal and a second pulse wave signal at the first measurement site O1 and the second measurement site O2, respectively.

The processor 220 may be included in the main body 100 and be electrically connected to the sensor 210. When a user's command or a predetermined condition is satisfied, the processor 220 may generate a control signal for controlling the sensor 210 to measure a biometric signal. In addition, the processor 220 may receive the biometric signals measured by the sensor 210, for example, the ECG, the first pulse wave signal, and the second pulse wave signal, and estimate biometric information using the received biometric signals. In this case, a separate operation unit which receives a user's command may be included in the main body 100, and if the display module has a touch input function, as described above, the user's command may be input through an interface provided by the display module.

The display 230 may display and provide information, such as the measured biometric signals, the estimated biometric information, biometric information-related alarming or warning information, and various interface screens, to the user.

Figure 4:
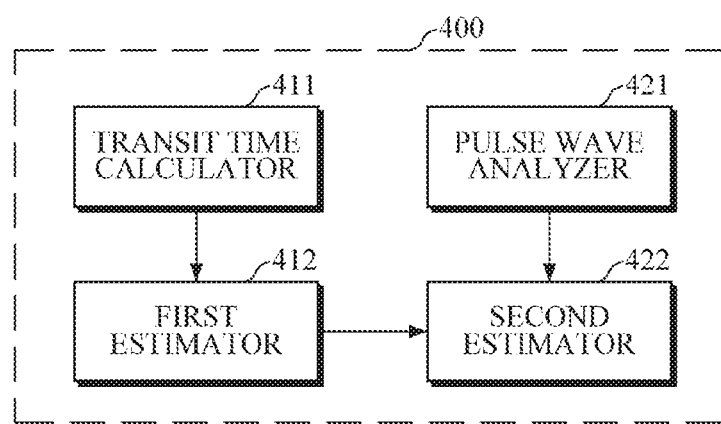
FIG. 4 is a block diagram illustrating a processor of the apparatus for estimating biometric information according to an exemplary embodiment.
Figure 5A:
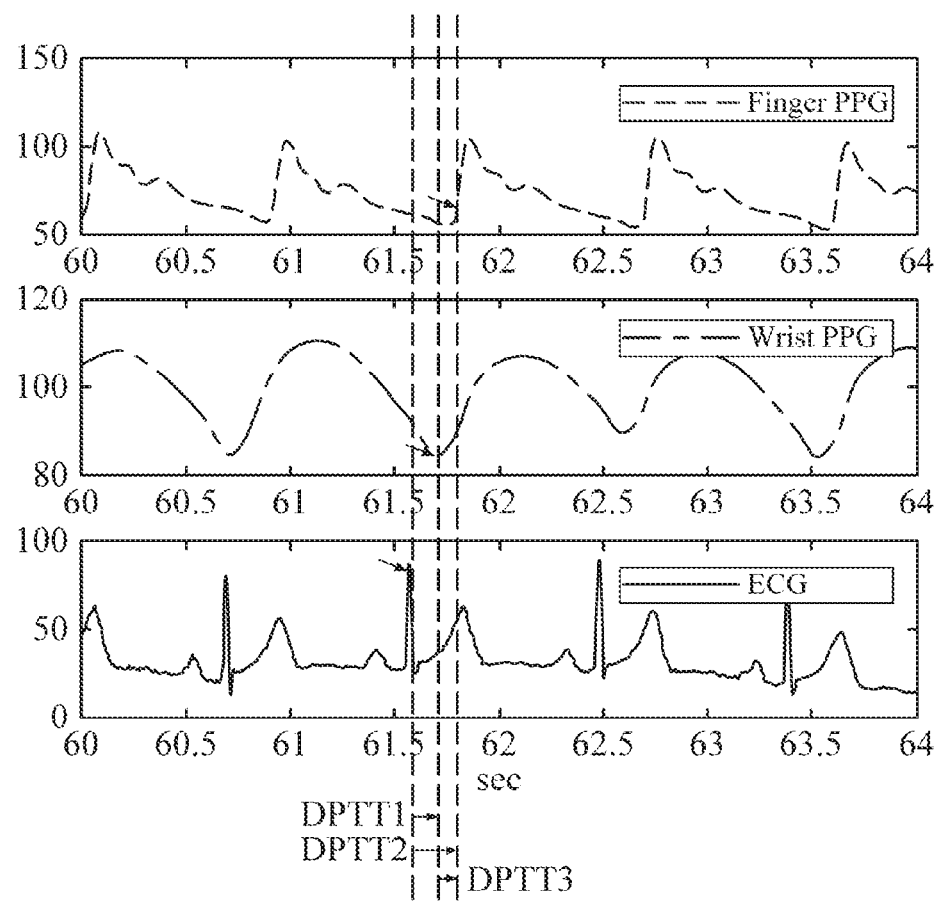
FIGS. 5A and 5B are diagrams for describing an example of biometric information estimation by the processor of FIG. 4.
Figure 5B:
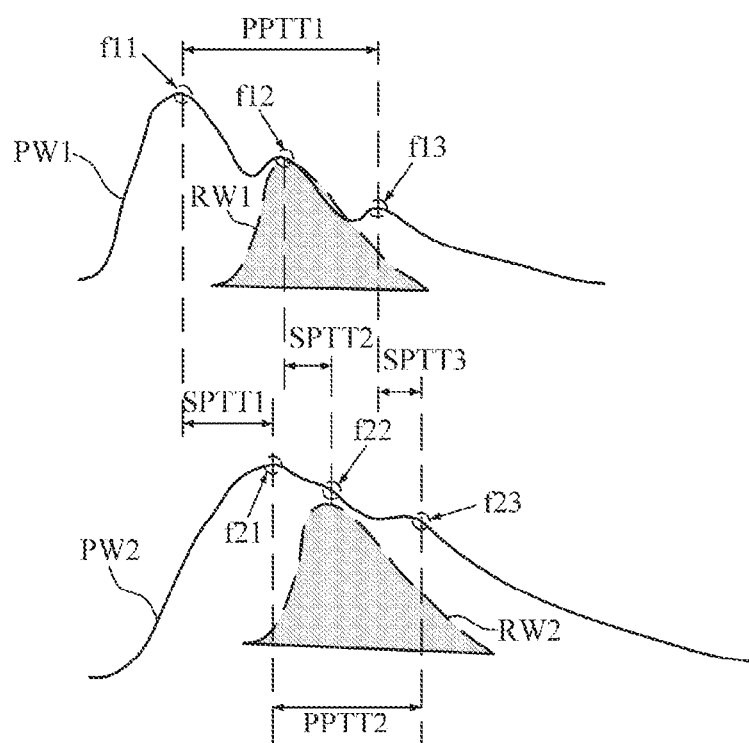

FIG. 4 is a block diagram illustrating the processor 220 of the apparatus 200 for estimating biometric information according to an exemplary embodiment. FIGS. 5A and 5B are diagrams for describing an example of biometric information estimation by the processor of FIG. 4.

One exemplary embodiment of a configuration of the processor 220 of the apparatus 200 for estimating biometric information will be described with reference to FIGS. 4 and 5B. As shown in FIG. 4, a processor 400 includes a transit time calculator 411, a first estimator 412, a pulse wave analyzer 421, and a second estimator 422.

When an ECG signal and two or more pulse wave signals are received from the sensor 210, the transit time calculator 411 may calculate three or more pulse transit time (PTT) using the received ECG and pulse wave signals. For example, referring to FIG. 5A, an ECG signal, a first pulse wave signal (i.e., Wrist PPG), a second signal (i.e., Finger PPG) are shown. The transit time calculator 411 may calculate a first differential pulse transit time DPTT1 using the ECG signal and the first pulse wave signal, calculate a second differential pulse transit time DPTT2 using the ECG signal and the second pulse wave signal, and calculate a third differential pulse transit time DPTT3 using the first pulse wave signal and the second pulse wave signal.

When the transit time calculator 411 has calculated three or more differential pulse transit times (DPTTs) including DPTT1, DPTT2, and DPTT3, the first estimator 412 may estimate first biometric information $BI_1$ by applying the three or more DPTTs to a first estimation model $F_1$, as shown in Equation 1 below. In this case, the first estimation module F1 may be in the form of a mathematical function expression, but the first estimation module is not limited thereto, and may be in the form of a table in which three or more PTT-based values (e.g., PTTs intact, an average thereof, etc.) and values of biometric information to be estimated are mapped to each other. In this case, the first biometric information may be a blood pressure, particularly, a diastolic blood pressure.

$$BI_1 = F_1(DPTT1, DPTT2, DPTT3) \quad (1)$$

In general, when biometric information, such as a blood pressure, is estimated, blood pressure estimate error due to pre-ejection period (PEP) exists in estimated blood pressure information because a single PTT calculated based on an ECG and one pulse wave signal is used in estimating. However, according to the present exemplary embodiment, in addition to the ECG and one pulse wave signal, two or more different pulse wave signals are used to calculate PTTs and the PTTs are applied to the estimation of blood pressure, so that the blood pressure estimate error due to the PEP can be reduced.

In addition, when the ECG and two or more pulse wave signals are received from the sensor 210, the pulse wave analyzer 421 may analyze degrees of impact of reflected waves on the pulse wave signals on the basis of the waveforms of the two or more pulse wave signals measured at multiple sites. For example, as shown in FIGS. 5A and 5B, the pulse wave analyzer 421 may extract feature points (e.g., inflection points of the waveform) of the waveforms of the pulse waves PW1 and PW2 and extract reflected wave characteristic information using the extracted feature points in order to analyze degrees of impact of the reflected waves RW1 and RW2 on the respective pulse wave signals PW1 and PW2. In this case, the pulse wave analyzer 421 may perform a second-order differentiation on each of the pulse wave signals PW1 and PW2, and extract a position of the pulse wave signal which corresponds to a time position corresponding to a local minimum point of the second-order differential signal as a feature point. Referring to FIG. 5B, it is seen that three feature points f11, f12, and f13 are extracted from the first wave signal PW1, and three feature points f21, f22, and f23 are extracted from the second pulse wave signal PW2.

When the feature points are extracted from each pulse wave signal PW1 and PW2, the pulse wave analyzer 421 may extract a first PTT or a second PTT as the reflected wave characteristic information using the feature points of the different pulse wave signals or the feature points of the same pulse wave signal. For example, as shown in FIG. 5B, the pulse wave analyzer 421 may extract three first PTTs SPTT1, SPTT2, and SPTT3 using time differences between the corresponding feature points f11-f21, f12-22, and f13-f23 between the first pulse wave signal PW1 and the second pulse wave signal PW2, and extract second PTTs PPTT1 and PPTT2 using a time difference between the feature points f11-f13 in the first pulse wave signal PW1 and a time difference between the feature points f21-f23 in the second pulse wave signal PW2.

When the reflected wave characteristic information is extracted, the second estimator 422 may extract second biometric information by applying the extracted reflected wave characteristic information to a second estimation model. In addition, the second estimation model may be in the form of a mathematical function expression like the first estimation model, but is not limited thereto. In this case, the second estimator 422 may estimate the second biometric information $BI_2$, as shown in the following Equation 2, by adding the first biometric information $BI_1$, which is estimated by the first estimator 412, to a calculation result obtained by applying the reflected wave characteristic information SPTT1, SPTT2, SPTT3, PPTT1, and PPTT2 to the second estimation model. In this case, the second biometric information may be blood pressure information, particularly, systolic blood pressure information.

$$BI_2=BI_1+F_2(SPTT1,SPTT2,SPTT3,PPTT1,PPTT2) \quad (2)$$

In general, in the case of a systolic blood pressure, a waveform of the pulse wave signal is considerably affected by a reflected wave. Therefore, according to the present exemplary embodiment, the systolic blood pressure is measured, separately from the measurement of a diastolic blood pressure, by applying the degree of impact of the reflected wave and thereby it is possible to reduce the estimation error.

Figure 6:
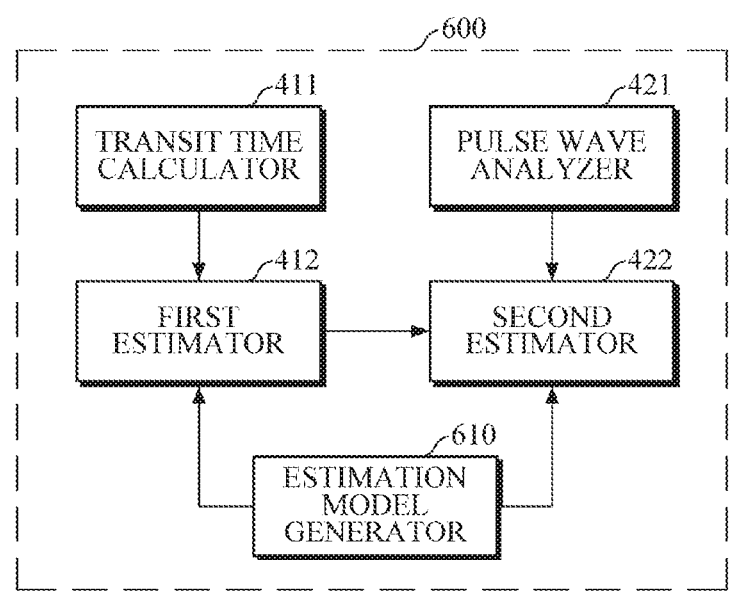
FIG. 6 is a block diagram illustrating a processor of an apparatus for measuring biometric information according to another exemplary embodiment.

FIG. 6 is a block diagram illustrating a processor of an apparatus for measuring biometric information according to another exemplary embodiment.

Referring to FIG. 6, the processor 600 may include a transit time calculator 411, a first estimator 412, a pulse wave analyzer 421, a second estimator 422, and an estimation model generator 610. The transit time calculator 411, the first estimator 412, the pulse wave analyzer 421, and the second estimator 422 are described above and thus detailed descriptions thereof will be omitted.

The estimator model generator 610 may generate or update an estimation model necessary for estimating biometric information, that is, the first estimation model and the second estimation model, which are described above, when a user's request or a predetermined condition is satisfied. The estimation model generator 610 may generate an estimation model at the time when the user registers to use the apparatus 200 for estimation biometric information for the first time. In addition, the estimation model generator 610 may generate or update the estimation model at the time point requested by the user or at a predetermined interval.

The estimation model generator 610 may receive personal information, such as age, sex, height, weight, health condition, and the like, from the user so that the user's personal characteristics can be applied to the estimation model. The user's personal information may be used as a factor to limit a value of biometric information to be estimated in the estimation model. For example, in estimating a blood pressure, such personal information may be used to limit the range of the maximum value and the minimum value of a blood pressure.

The estimation model generator 610 may control the sensor 210 to measure biometric signals for a predetermined time (e.g., 4 hours) at a predetermined interval (e.g., 15 minutes) in response to an estimation model generation request, and collect measured biometric signals as learning data. The estimation model generator 610 may also collect, as learning data, a value of actual biometric information estimated by an external apparatus for estimating biometric information, for example, a blood pressure measured by a cuff-type blood pressure measuring device. However, the exemplary embodiment is not limited to the above examples, and the user's various information of the user, such as a peripheral vascular resistance value, blood viscosity, a stroke volume, and the like, may be collected as learning data.

The estimation model generator 610 may generate or update the estimation model using the collected personal information and learning data.

Figure 7:
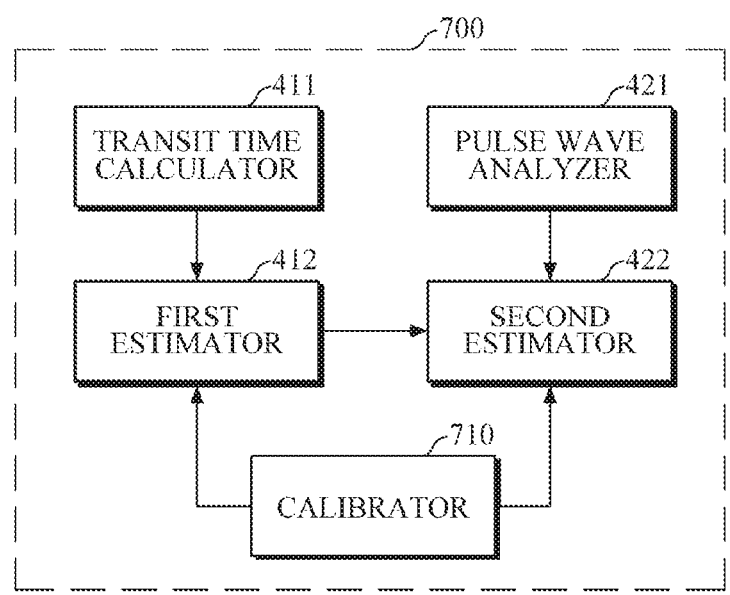
FIG. 7 is a block diagram illustrating a processor of an apparatus for estimation biometric information according to still another exemplary embodiment.
Figure 8:
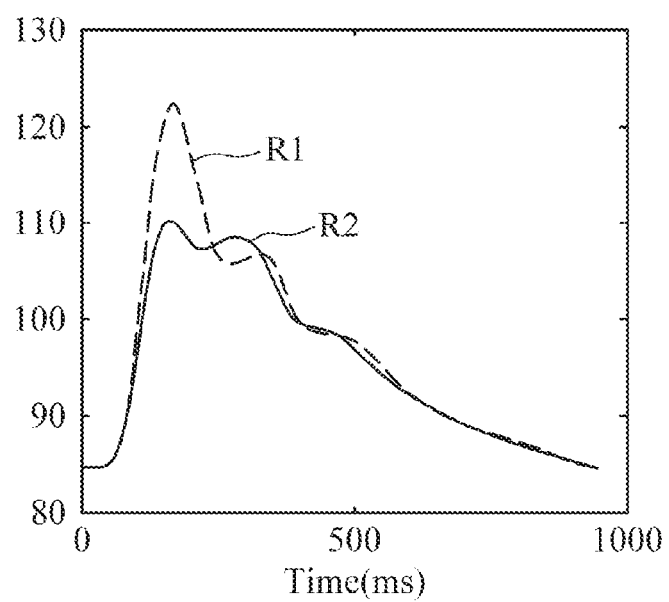
FIG. 8 is a diagram for describing an example in which the processor of FIG. 7 calibrates biometric information.

FIG. 7 is a block diagram illustrating a processor of an apparatus for estimation biometric information according to still another exemplary embodiment. FIG. 8 is a diagram for describing an example in which the processor of FIG. 7 calibrates biometric information.

Referring to FIG. 7, the processor 700 according to the present exemplary embodiment includes a transit time calculator 411, a first estimator 412, a pulse wave analyzer 421, a second estimator 422, and a calibrator 710. The transit time calculator 411, the first estimator 412, the pulse wave analyzer 421, and the second estimator 422 are described above, and hence detailed descriptions thereof will be omitted.

The calibrator 710 may estimate additional information using two or more pulse wave signals measured by the sensor 210, and may allow the first estimator 412 and the second estimator 422 to further estimate first biometric information and second biometric information, respectively, by taking into consideration the estimated additional information. Alternatively, when a model that represents a correlation between the first and second biometric information and the additional information is established in advance, the calibrator 710 may directly calibrate the first biometric information and the second biometric information using the additional information. In this case, the additional information includes information, such as a peripheral vascular resistance value, but is not limited thereto.

For example, the calibrator 710 may estimate the pattern of blood vessel wave propagation using the waveforms of a first pulse wave signal and a second pulse wave signal measured by the sensor 210, and may obtain information, such as a peripheral vascular resistance value, by applying the estimated propagation pattern to a vascular resistance estimation model. In this case, the vascular resistance estimation model may be generated for which a vascular resistance estimation model representing the pattern of the blood vessel wave propagation from the aorta to the radial artery and the carotid artery is fitted to the propagation patterns of the first pulse wave signal measured at a wrist and the second pulse wave signal measured at a finger.

With reference to FIG. 8, waveform R1 indicates a waveform when that is generated when the resistance of a peripheral blood vessel of a hand is 0, and waveform R2 shows a degree of deformation of the waveform R1 that is deformed due to the resistance of the peripheral blood vessel. The waveforms R1 and R2 may be applied to the vascular resistance estimation model to estimate the peripheral vascular resistance value. For example, the calibrator 710 may assume that the waveform of the first pulse wave signal measured at the wrist is a waveform when there is no resistance (e.g., waveform R1) and the waveform of the second pulse wave signal measured at the finger is a waveform when there is a resistance (e.g., waveform R2), and apply a difference between the two waveforms (e.g., waveforms R1 and R2) to the vascular resistance estimation model to estimate the peripheral vascular resistance information.

In this case, the first estimator 412 may estimate the first biometric information by applying the PTTs PTT1, PTT2, and PTT3 measured by the transit time calculator 411 and peripheral vascular resistance information TPR to a first estimation model $F_1$, as shown in Equation 3.

$$BI_1 = F_1(DPTT1, DPTT2, DPTT3, TPR) \quad (3)$$

In the same manner, the second estimator 422 may estimate the second biometric information by applying the reflected wave characteristic information PPTT1, PPTT2, SPTT1, SPTT2, and SPTT3 measured by the pulse wave analyzer 421 and the peripheral vascular resistance information TPR to a second estimation model $F_2$, as shown in Equation 4.

$$BI_2 = F_2(SPTT1, SPTT2, SPTT3, PPTT1, PPTT2, TPR) \quad (4)$$

Figure 9:
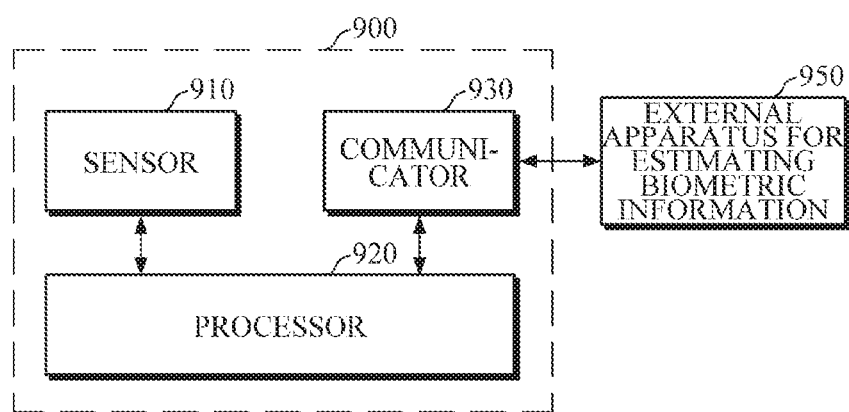
FIG. 9 is a block diagram illustrating an apparatus for estimating biometric information according to another exemplary embodiment.
Figure 10:
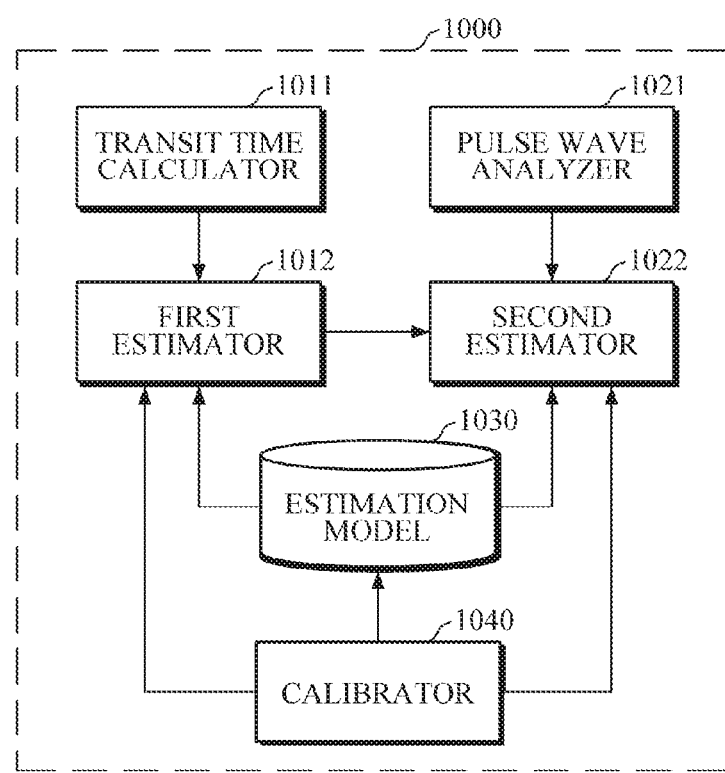
FIG. 10 is a block diagram illustrating a configuration of a processor according to the exemplary embodiment of FIG. 9.
Figure 11:
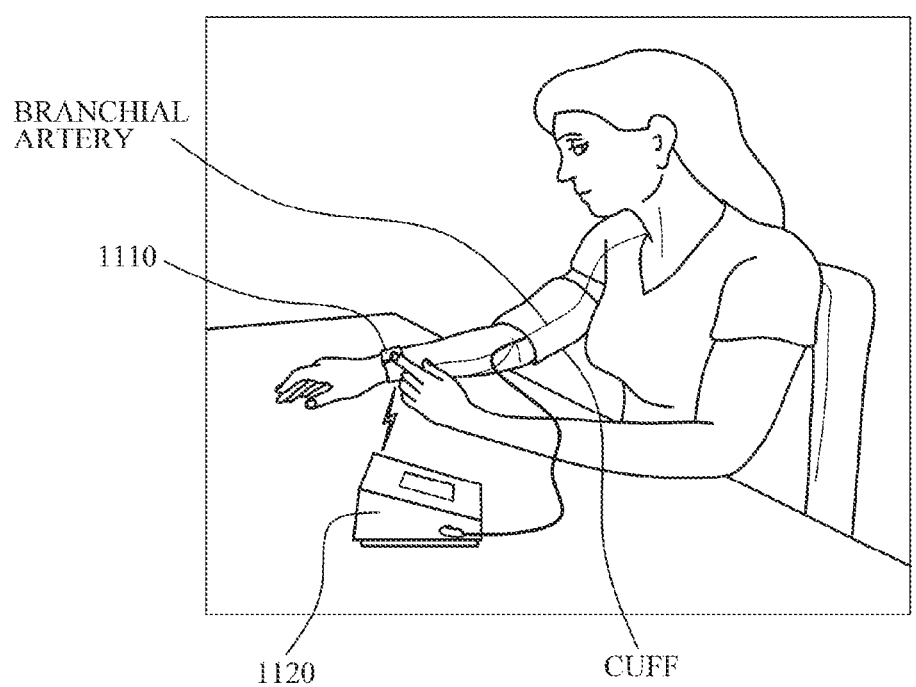
FIG. 11 is a diagram for describing an example in which the apparatus of FIG. 9 calibrates biometric information.

FIG. 9 is a block diagram illustrating an apparatus for estimating biometric information according to another exemplary embodiment. FIG. 10 is a block diagram illustrating a configuration of a processor according to the embodiment of FIG. 9. FIG. 11 is a diagram for describing an example in which the apparatus of FIG. 9 calibrates biometric information. The apparatus 900 for estimating biometric information according to the present embodiment may be another exemplary embodiment of the apparatus 1 shown in FIGS. 1A and 1B.

Referring to FIG. 9, the apparatus 900 for estimating biometric information includes a sensor 910, a processor 920, and a communicator 930. The communicator 903 may be implemented with a communication interface. The apparatus 900 according to the present exemplary embodiment may receive reference biometric information from an external apparatus for estimating biometric information and calibrate current biometric information using the received reference biometric information. The sensor 910 may include an ECG sensor and two or more pulse wave sensors, as described with reference to FIG. 3, and may measure an ECG and a pulse wave signal at two or more measurement sites. The processor 920 includes a transit time calculator 1011, a first estimator 1012, a pulse wave analyzer 1021, a second estimator 1022, an estimation model 1030, and a calibrator 1040, and estimates biometric information using biometric signals measured by the sensor 910. The sensor 910 and the processor 920 have been described in detail above and thus the following description will focus on functions that are not stated.

The processor 920 may communicate with external apparatus 950 for estimating biometric information by controlling the communicator 930 in response to a user's calibration command. In this case, the communication technology may include, but is not limited to, a Bluetooth communication, Bluetooth low energy (BLE) communication, a near-field communication (NFC), a wireless local area network (WLAN) communication, a ZigBee communication, an infrared data association (IrDA) communication, a Wi-Fi direct (WFD) communication, a ultra-wideband (UWB) communication, an Ant+ communication, a Wi-Fi communication, and a mobile communication.

When the communication connection to the external apparatus 950 for estimating biometric information is successful, the processor 920 controls the sensor 910 to measure a biometric signal of the user while the external apparatus 950 estimates the biometric information of the user. However, the exemplary embodiment is not limited to the case where the external apparatus 950 is operated at the same time.

When the biometric signal is estimated by the sensor 910, the transit time calculator 1011 and the first estimator 1012 may estimate first biometric information and the pulse wave analyzer 1021 and the second estimator 1022 may estimate second biometric information.

When the external apparatus 950 for estimating biometric information completes estimating the biometric information, the communicator 930 may receive the estimated biometric information as reference biometric information and forward the biometric information to the calibrator 1040.

The calibrator 1040 may calibrate the values of biometric information estimated by the first estimator 1012 and the second estimator 1022 using the received reference biometric information. Alternatively, the calibrator 1040 may calibrate the estimation model 1030 required to estimate the biometric information. In this case, the estimation model 1030 may be stored in a storage module as a first estimation model and a second estimation model. The storage module may include at least one type of memory, such as a flash memory, a hard disk, a micro type multimedia card, and a card type memory (e.g., SD or XD memory), a random access memory (RAM), a static random access memory (SRAM), a read only memory (ROM), an electrically erasable programmable read only memory (EEPROM), a programmable read only memory (PROM), a magnetic memory, a magnetic disk, and an optical disk, but is not limited thereto.

Alternatively, the calibrator 1040 may calibrate the PTTs calculated by the transit time calculator 1011 and the reflected wave characteristic information acquired by the pulse wave analyzer 1021. In this case, the external apparatus 950 may be a cuff-type blood pressure measuring device, and the reference biometric information may include measured blood pressure information and cuff pressure information measured at multiple sites.

For example, referring to FIG. 11, when the user inputs a calibration command while wearing the wristwatch-type cuffless blood pressure estimating apparatus 1110, the cuffless blood pressure estimating apparatus 1110 may be connected with a cuff-type blood pressure measuring apparatus 1120 to receive blood pressure information or cuff pressure information, and calibrate information related to the blood pressure information estimated by the cuffless blood pressure estimating apparatus 110, using the received blood pressure information or cuff pressure information.

Figure 12:
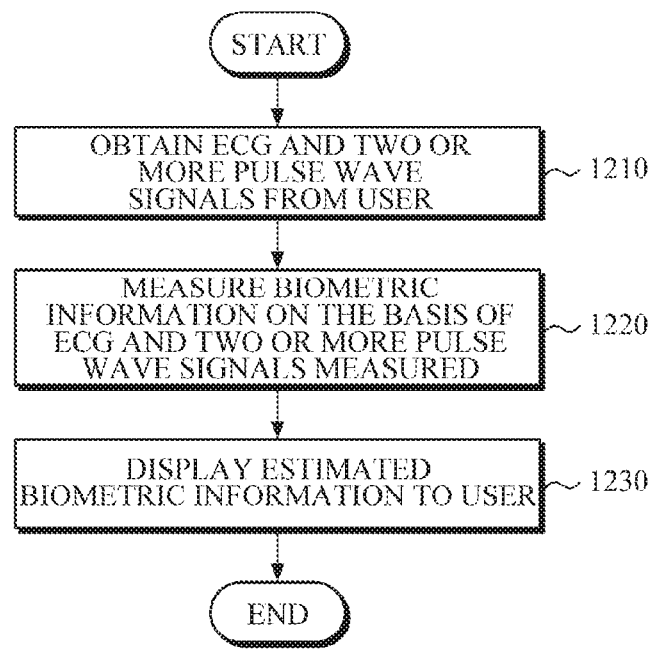
FIG. 12 is a flowchart illustrating a method of estimating biometric information according to an exemplary embodiment.
Figure 13:
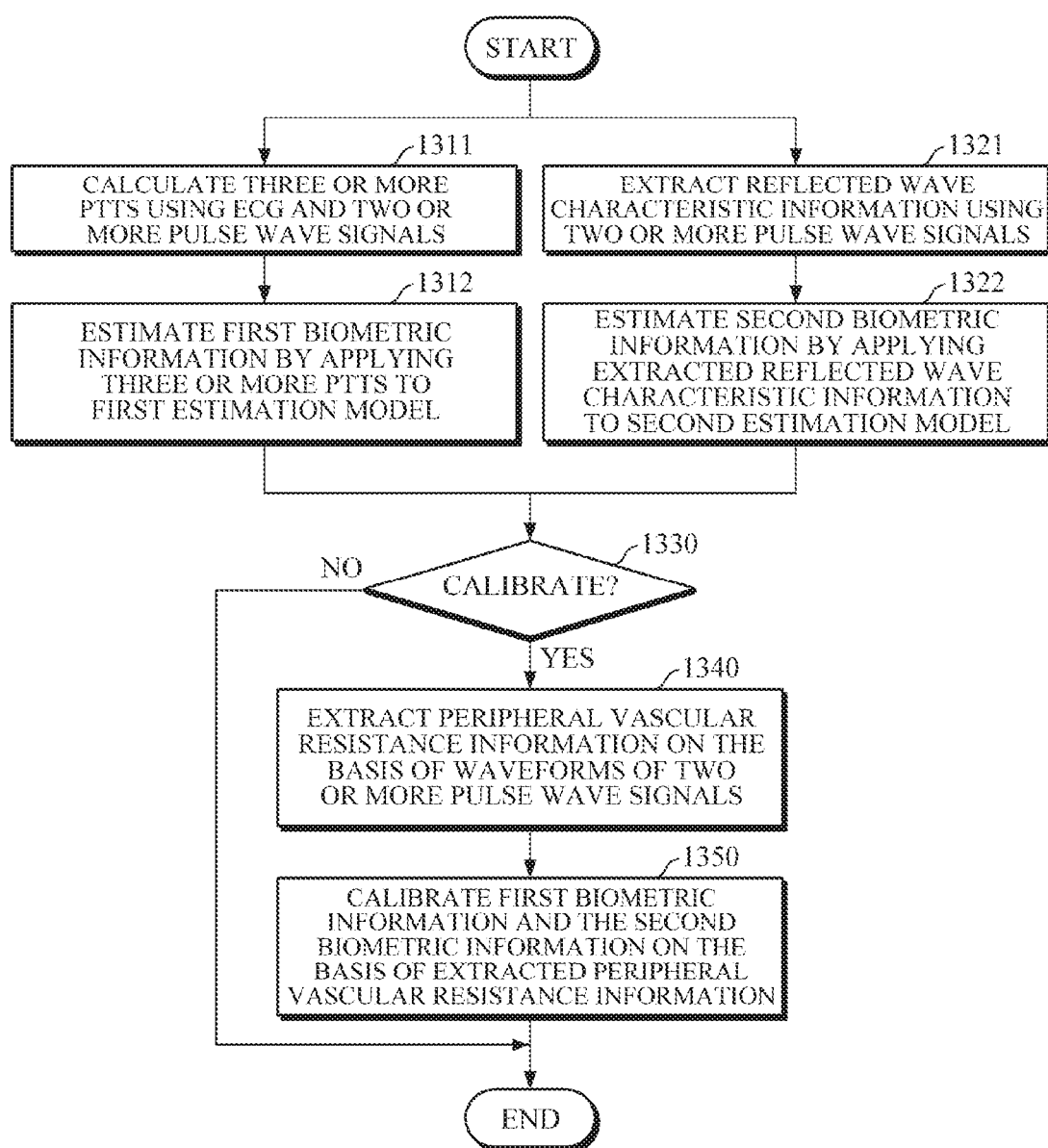
FIG. 13 is a flowchart illustrating one embodiment of estimation of biometric information in the method of FIG. 12.

FIG. 12 is a flowchart illustrating a method of estimating biometric information according to an exemplary embodiment. FIG. 13 is a flowchart illustrating one embodiment of estimation of biometric information in the method of FIG. 12. The method of FIG. 12 may be one embodiment of a biometric information estimation method performed by the apparatus 200 of FIG. 2. Since the operations have been described in detail above, a brief description will be made in order to minimize redundant description.

First, the apparatus 200 for estimating biometric information obtains an ECG signal and two or more pulse wave signals from a user in operation 1210. According to one embodiment, the apparatus 200 may include an ECG sensor and two or more pulse wave sensors to measure biometric signals at a plurality of sites so that biometric information can be estimated using a plurality of biometric signals, for example, an ECG signal and pulse wave signals.

Then, when the ECG and the two or more pulse wave signals are measured, the biometric information is estimated using the ECG signal and two or more pulse wave signals measured in operation 1220. The biometric information may be displayed to the user in operation 1230.

One exemplary embodiment of operation 1220 of the biometric information estimation will be described in detail with reference to FIG. 13. First, three or more PTTs are calculated using the ECG signal and two or more pulse wave signals measured in operation 1311.

Then, first biometric information is estimated by applying the calculated three or more PTTs to a first estimation model, in operation 1312. According to the present exemplary embodiment, the first biometric information, for example, a diastolic blood pressure, is estimated by taking into consideration the PTTs which have been calculated using different pulse wave signals, and thereby it is possible to reduce blood pressure estimation error due to PEP.

In addition, when the ECG and two or more pulse wave signals are obtained in operation 1210, reflected wave characteristic information is extracted using the two or more pulse wave signals in operation 1321. For example, feature points may be extracted from a first pulse wave signal and a second pulse wave signal, a PTT may be calculated using feature points of both the first and second pulse wave signals, a PTT may be calculated using the feature points in the first pulse wave signal and the feature points in the second pulse wave signal, and the calculated PTTs may be extracted as the reflected wave characteristic information.

Thereafter, second biometric information is estimated by applying the extracted reflected wave characteristic information to a second estimation model in operation 1322. In this case, the second biometric information may be a systolic blood pressure. The systolic blood pressure may be calculated as a value of the second biometric information by adding the value of first biometric information estimated in operation 1312 to a value obtained by applying the extracted reflected wave characteristic information to the second estimation model.

Then, it is determined whether it is needed to calibrate the biometric information using additional information in operation 1330. In this case, whether or not the biometric information calibration is necessary may be set in advance based on various types of information, such as a required accuracy of the biometric information estimation, a battery status of the apparatus, a type of biometric information, and the like. For example, in a case where it is necessary to estimate biometric information more accurately even if a relatively long time is required to estimate the biometric information, for example, in the case of a patient having a disease, such as hypertension or hypotension, calibration in consideration of additional information, such as peripheral vascular resistance information, may be necessary.

Then, when it is determined that the calibration is necessary, peripheral vascular resistance information is extracted by analyzing waveforms of the two or more pulse wave signals in operation 1340. Then, the first biometric information and the second biometric information are calibrated based on the extracted peripheral vascular resistance information in operation 1350.

However, FIG. 13 illustrates that operations 1330, 1340 and 1350 are performed after operations 1312 and 1322 are completed, but the exemplary embodiment is not limited thereto. Operations 1330 and 1340 may be performed before operations 1312 and 1322. In this case, the first biometric information may be estimated based on the extracted peripheral vascular resistance information together with the PTTs in operation 1312 and the second biometric information may be estimated based on the reflected wave characteristic information in operation 1322.

Figure 14:
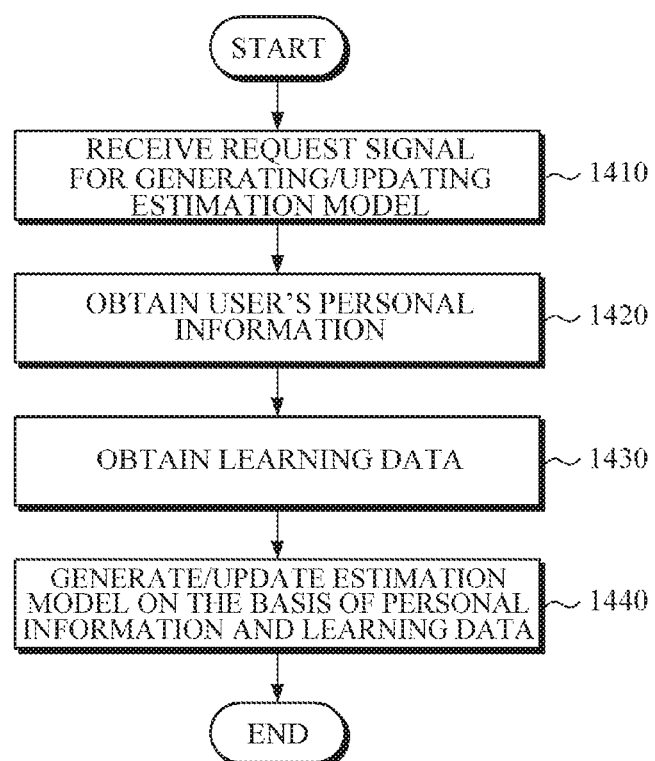
FIG. 14 is a flowchart illustrating a method of estimating biometric information according to another exemplary embodiment.

FIG. 14 is a flowchart illustrating a method of estimating biometric information according to another exemplary embodiment.

The method of FIG. 14 may be one exemplary embodiment of a biometric information estimation method performed by the apparatus 200 to which the exemplary embodiment of the processor 600 of FIG. 6 is applied. FIG. 14 separately shows a process of generating or updating an estimation model for estimating biometric information, but the process may be performed in parallel with or before the operations described with reference to FIGS. 12 and 13.

The apparatus 200 for estimating biometric information receives a request signal for generating or updating an estimation model from a user or determines whether to generate or update the estimation model by checking specific conditions set in advance, in operation 1410.

Then, personal information for applying personal characteristics is received from the user in operation 1420. In this case, the personal information may be applied to an estimation model so that biometric information can be more accurately estimated in consideration of the health condition and age of the user.

Then, biometric signals, such as an ECG and pulse wave signals, are collected as learning data by controlling a sensor for a predetermined time period in operation 1430. In this case, cuff blood pressure information measured by a cuff-type blood pressure measuring device may be additionally collected as learning data. However, the present exemplary embodiment is not limited to the above-described information, and various types of additional information, such as peripheral vascular resistance information, blood viscosity, a stroke volume, and the like, may be collected as learning data.

Thereafter, an estimation model is generated or updated using the personal information and the learning data in operation 1440.

Figure 15:
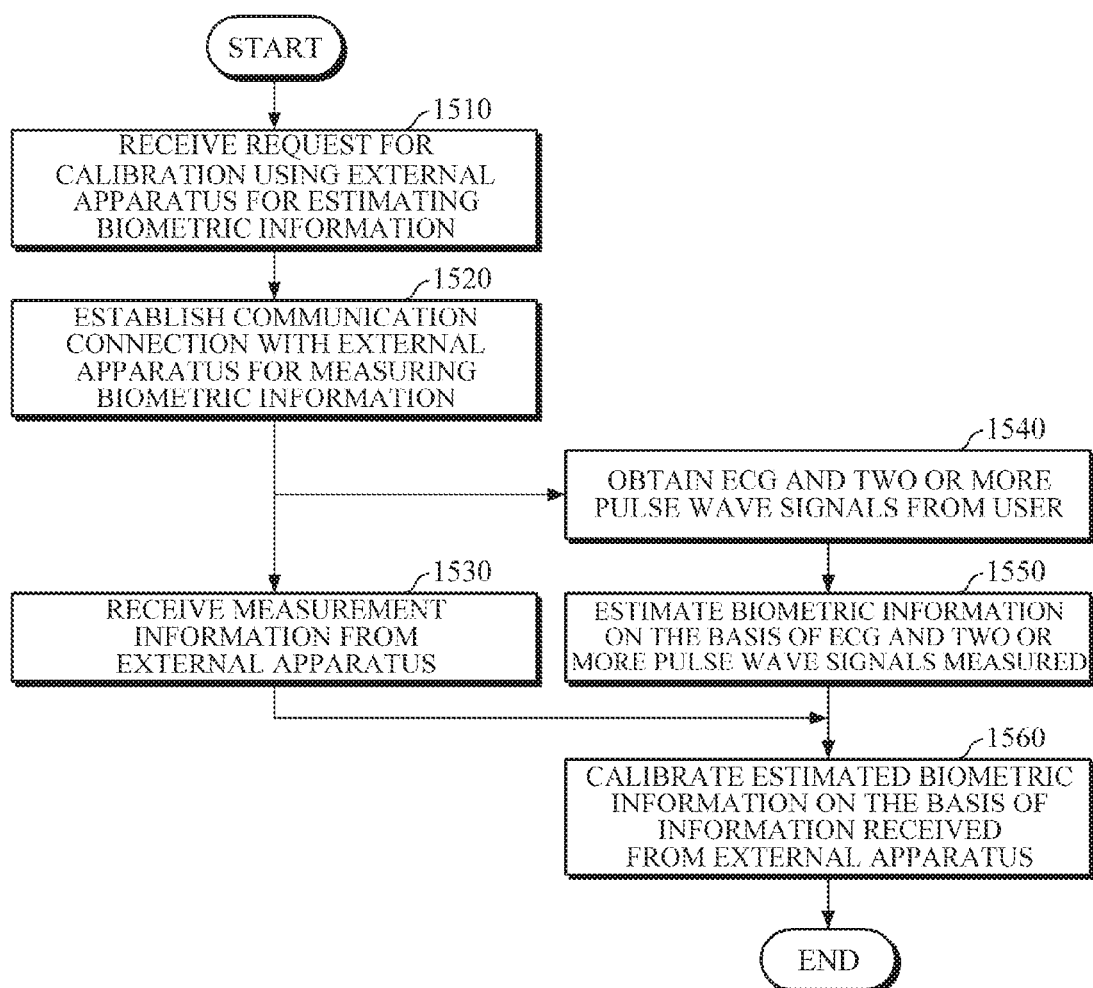
FIG. 15 is a flowchart illustrating a method of estimating biometric information according to still another exemplary embodiment.

FIG. 15 is a flowchart illustrating a method of estimating biometric information according to still another exemplary embodiment.

The method of FIG. 15 is one exemplary embodiment of a biometric information calibration method performed by the apparatus 900 for estimating biometric information shown in FIG. 9.

First, the apparatus 900 receives, from a user, a request for calibration using an external apparatus for estimating biometric information in operation 1510.

Then, the apparatus 900 is connected to the external apparatus via wired or wireless communication in operation 1520, and receives reference biometric information measured when the external apparatus completes the measurement in operation 1530. In this case, the external apparatus may be a cuff-type blood pressure measuring apparatus, and the reference biometric information may include a blood pressure and cuff pressure information.

Also, when the communication connection with the external apparatus is completed, the apparatus 900 obtains an ECG signal and pulse wave signals by controlling a sensor in operation 1540. At this time, the sensor may obtain two or more pulse wave signals from two measurement sites, e.g., a wrist and a finger.

Then, biometric information is estimated on the basis of the ECG signal and two or more pulse wave signals measured in operation 1560. As described above, first biometric information (e.g., a diastolic blood pressure) may be estimated by calculating PTTs using the ECG signal and two or more pulse wave signals, and second biometric information (e.g., a systolic blood pressure) may be estimated using reflected wave characteristics of the two or more pulse wave signals.

Then, the first biometric information and the second biometric information, which are estimated on the basis of the reference biometric information received from the external apparatus, are calibrated in operation 1560. In FIG. 5, operation 1560 is described as being performed after operation 1550, but this is merely an example. An estimation model may be calibrated using the reference biometric information before operation 1550 or the biometric information may be estimated in operation 1550 after the PTTs or the reflected wave characteristic information is calibrated.

While not restricted thereto, an exemplary embodiment can be implemented as computer readable codes in a computer readable record medium. The computer-readable recording medium is any data storage device that can store data that can be thereafter read by a computer system. The computer readable record medium includes all types of record media in which computer readable data are stored. Examples of the computer readable record medium include a read-only memory (ROM), a random-access memory (RAM), a compact disk ROM (CD-ROM), a magnetic tape, a floppy disk, and an optical data storage. Further, the record medium may be implemented in the form of a carrier wave such as Internet transmission. In addition, the computer readable record medium may be distributed to computer systems over a network, in which computer readable codes may be stored and executed in a distributed manner. Also, an exemplary embodiment may be written as a computer program transmitted over a computer-readable transmission medium, such as a carrier wave, and received and implemented in general-use or special-purpose digital computers that execute the programs. Moreover, it is understood that in exemplary embodiments, one or more units of the above-described apparatuses and devices can include circuitry, a processor, a microprocessor, etc., and may execute a computer program stored in a computer-readable medium.

The foregoing exemplary embodiments are merely exemplary and are not to be construed as limiting. The present teaching can be readily applied to other types of apparatuses. Also, the description of the exemplary embodiments is intended to be illustrative, and not to limit the scope of the claims, and many alternatives, modifications, and variations will be apparent to those skilled in the art.

What is claimed is:

1. A wearable device for estimating biometric information comprising:
   a main body;
   an electrocardiogram (ECG) sensor comprising:
      a first electrode disposed on a front surface of the main body to be in contact with a finger of a user; and
      a second electrode disposed on a rear surface of the main body to be in contact with a wrist of the user when the wearable device is worn by the user,
      wherein the ECG sensor is configured to measure an ECG signal of the user using the first electrode and the second electrode,
   a first pulse wave sensor disposed on the front surface of the main body and configured to measure a finger photoplethysmogram (PPG) signal at the finger;
   a second pulse wave sensor disposed on the rear surface of the main body and configured to measure a wrist PPG signal at the wrist; and
   a processor configured to obtain a first differential pulse transit time between a first point in time in the ECG signal and a second point in time in the finger PPG signal, a second differential pulse transit time between the first point in time in the ECG signal and a third point in time in the wrist PPG signal, and a third differential pulse transit time between the second point in time in the finger PPG signal and the third point in time in the wrist PPG signal, and obtain the biometric information based on the first differential pulse transit time, the second differential pulse transit time, and the third differential pulse transit time.

2. The wearable device of claim 1, further comprising:
   a strap connected to the main body and formed to be flexible to wrap around the wrist.

3. The wearable device of claim 1, wherein the first electrode and the second electrode correspond to a positive electrode and a negative electrode of the ECG sensor, respectively.

4. The wearable device of claim 1, wherein the first electrode and the second electrode correspond to a negative electrode and a positive electrode of the ECG sensor, respectively.

5. The wearable device of claim 1, wherein
   the biometric information is a blood pressure level of the user.

6. The wearable device of claim 1, wherein the biometric information comprises first biometric information, and
   wherein the processor is further configured to apply the first differential pulse transit time, the second differential pulse transit time, and the third differential pulse transit time to a first estimation model to obtain the first biometric information.

7. The wearable device of claim 6, wherein the biometric information further comprises second biometric information, and
   wherein the processor is further configured to:
      extract, from the finger PPG signal and the wrist PPG signal, reflected wave characteristic information indicating an impact of reflected waves of the finger PPG signal and the wrist PPG signal on a change in waveform of the finger PPG signal and the wrist PPG signal, and
      apply the extracted reflected wave characteristic information to a second estimation model to obtain the second biometric information.

8. The wearable device of claim 7, wherein the processor is further configured to:
   extract feature points from the finger PPG signal and the wrist PPG signal, and
   extract the reflected wave characteristic information which comprises the first differential pulse transit time, the second differential pulse transit time, and the third differential pulse transit time.

9. The wearable device of claim 7, wherein when a result is output by applying the extracted reflected wave characteristic information to the second estimation model, the processor is further configured to obtain the second biometric information based on the output result and the first biometric information.

10. The wearable device of claim 9, wherein the first biometric information is a diastolic blood pressure and the second biometric information is a systolic blood pressure.

11. The wearable device of claim 1, wherein the processor is further configured to generate an estimation model for estimating the biometric information based on personal information input by the user, and the personal information comprises one or more of height, weight, sex, age, and a health condition of the user.

12. The wearable device of claim 1, wherein the processor is further configured to obtain vascular resistance information based on waveforms of the finger PPG signal and the wrist PPG signal and calibrate the biometric information based on the vascular resistance information.

13. The wearable device of claim 1, further comprising:
a communication interface configured to receive reference biometric information from an external apparatus;
wherein the processor is further configured to calibrate the biometric information based on the reference biometric information.

14. The wearable device of claim 13, wherein the processor is further configured to obtain the biometric information while the external apparatus obtains the reference biometric information of the user.

15. The wearable device of claim 13, wherein the processor is further configured to calibrate at least one of a value of the biometric information, the first differential pulse transit time, the second differential pulse transit time, the third differential pulse transit time, and an estimation model for estimating the biometric information.

16. The wearable device of claim 13, wherein the external apparatus comprises a cuff-type blood pressure estimating apparatus and the reference biometric information comprises at least one of a cuff blood pressure estimated by the cuff-type blood pressure estimating apparatus and cuff pressure information.

17. A method of estimating biometric information by a wearable device, the method comprising:
measuring an electrocardiogram (ECG) signal of a user by using a first electrode that is disposed on a front surface of a main body of the wearable device to be in contact with a finger of the user, and a second electrode that is disposed on a rear surface of the main body to be in contact with a wrist of the user when the wearable device is worn by the user;
measuring a finger photoplethysmogram (PPG) signal at the finger using a first pulse wave sensor disposed on the front surface of the main body;
measuring a wrist PPG signal at the wrist by using a second pulse wave sensor disposed on the rear surface of the main body;
obtaining a first differential pulse transit time between a first point in time in the ECG signal and a second point in time in the finger PPG signal, a second differential pulse transit time between the first point in time in the ECG signal and a third point in time in the wrist PPG signal, and a third differential pulse transit time between the second point in time in the finger PPG signal and the third point in time in the wrist PPG signal; and
obtaining the biometric information based on the first differential pulse transit time, the second differential pulse transit time, and the third differential pulse transit time.

18. The method of claim 17, wherein the biometric information comprises first biometric information and second biometric information, and
wherein the obtaining the biometric information comprises:
applying the first differential pulse transit time, the second differential pulse transit time, and the third differential pulse transit time to a first estimation model to obtain the first biometric information;
extracting, from waveforms of the finger PPG signal and the wrist PPG signal, reflected wave characteristic information indicating an impact of reflected waves of the finger PPG signal and the wrist PPG signal on a change in waveform of the finger PPG signal and the wrist PPG signal, and
applying the extracted reflected wave characteristic information to a second estimation model to obtain the second biometric information.

19. The method of claim 18, wherein when a result is output by applying the extracted reflected wave characteristic information to the second estimation model, the second biometric information is obtained based on the output result and the first biometric information.

20. The method of claim 17, further comprising:
receiving personal information input by the user, the personal information comprising one or more of height, weight, sex, age, and a health condition of the user; and
generating an estimation model for estimating the biometric information based on the received personal information.

21. The method of claim 17, further comprising:
obtaining vascular resistance information based on waveforms of the finger PPG signal and the wrist PPG signal; and
calibrating the biometric information based on the vascular resistance information to correct an error in the biometric information.

22. The method of claim 17, further comprising:
receiving reference biometric information from an external apparatus; and
calibrating the biometric information based on the received reference biometric information.

23. The method of claim 22, wherein the calibrating the biometric information comprises calibrating at least one of a value of the biometric information, the first differential pulse transit time, the second differential pulse transit time, the third differential pulse transit time, and an estimation model for estimating the biometric information.

24. The method of claim 22, wherein the reference biometric information comprises at least one of a cuff blood pressure estimated by a cuff-type blood pressure estimating apparatus included in the external apparatus and cuff pressure information.

* * * * *